(12) United States Patent
Firgo et al.

(10) Patent No.: US 8,633,120 B2
(45) Date of Patent: Jan. 21, 2014

(54) LYOCELL FIBER

(75) Inventors: Heinrich Firgo, Vöcklabruck (AT); Heidrun Fuchs, Vöcklabruck (AT)

(73) Assignee: Lenzing Aktiengesellschaft, Lenzing (AT)

( * ) Notice: Subject to any disclaimer, the term of this patent is extended or adjusted under 35 U.S.C. 154(b) by 0 days.

(21) Appl. No.: 12/678,610

(22) PCT Filed: Sep. 15, 2008

(86) PCT No.: PCT/AT2008/000329
§ 371 (c)(1), (2), (4) Date: Jun. 11, 2010

(87) PCT Pub. No.: WO2009/036481
PCT Pub. Date: Mar. 26, 2009

(65) Prior Publication Data
US 2010/0248572 A1    Sep. 30, 2010

(30) Foreign Application Priority Data
Sep. 18, 2007  (AT) ................................ A 1457/2007

(51) Int. Cl.
*B32B 5/16* (2006.01)
*B32B 19/00* (2006.01)

(52) U.S. Cl.
USPC ............ 442/417; 428/357; 428/365; 428/402

(58) Field of Classification Search
USPC ............ 442/191, 417; 428/372, 357, 365, 402
See application file for complete search history.

(56) References Cited

U.S. PATENT DOCUMENTS

| 4,246,221 | A | 1/1981 | McCorsley, III | 264/203 |
| 4,783,975 | A * | 11/1988 | Komatsu et al. | 63/32 |
| 7,951,237 | B2 | 5/2011 | Zikeli et al. | 106/162.2 |
| 2003/0186611 | A1 | 10/2003 | Zikeli et al. | 442/361 |
| 2007/0161311 | A1 | 7/2007 | Zikeli et al. | 442/181 |

FOREIGN PATENT DOCUMENTS

| CN | 1450212 A | | 10/2003 |
| CN | 1772980 A | * | 5/2006 |
| CN | 1986917 A | | 6/2007 |
| DE | 100 07 794 A1 | | 6/2001 |
| DE | 103 30 292 A1 | | 2/2005 |
| DE | 10 2005 044 002 A1 | | 3/2007 |
| EP | 1 259 564 B1 | | 11/2002 |
| EP | 1 657 258 A1 | | 5/2006 |
| GB | 1 360 925 | | 5/1972 |
| JP | 2006-241627 | | 9/2006 |
| WO | WO 2005/017247 A2 | | 2/2005 |

OTHER PUBLICATIONS

Hongu and Phillips, New Fibers, 1997, Woodhead Publishing, second edition, chapter 8, p. 194.*
Translation of the Written Opinion of the International Searching Authority issued in the International Application No. PCT/At 2008/000329—5 pages, Mar. 17, 2010.
Perle—de.wikipedia.org/wiki/Perle—11 pages, May 18, 2010.
Perlmutt—de.wikipedia.org/wiki/Perlmutt—3 pages, May 18, 2010.
Kari Pearls —www.karipearl.com/medicine.html—5 pages.
"Rayon," Nordic, Initiative, Clean and Ethical (professional guide)—www.nicefashion.org/en/professional-guide/production/viscose.html—2 pages.

* cited by examiner

*Primary Examiner* — Lynda Salvatore
(74) *Attorney, Agent, or Firm* — Fitzpatrick, Cella, Harper & Scinto

(57) ABSTRACT

The invention concerns a Lyocell fiber, containing a material selected from the group consisting of pearl powder, ground nacre and mixtures thereof. For the manufacture of the fiber according to the invention, a process is used comprising the steps of
    manufacturing a spinning solution of cellulose in an aqueous tertiary amine oxide, preferably N-methylmorpholine-N-oxide (NMMO)
    spinning the spinning solution to fibers,
and being characterized in that a material selected from the group consisting of pearl powder, ground nacre and mixtures thereof is admixed to the spinning solution and/or to a precursor thereof.

11 Claims, No Drawings

LYOCELL FIBER

BACKGROUND OF THE INVENTION

Fibers of the Lyocell genus are produced by a solvent-spinning process, wherein the cellulose is dissolved directly in an aqueous tertiary amine-oxide without the formation of a derivative, and the solution is spun. Such fibers are also referred to as "solvent-spun" fibers. "Lyocell" is the generic name allocated by BISFA (The International Bureau for the Standardization of man made fibers) for cellulose fibers which are produced by dissolving cellulose in an organic solvent without the formation of a derivative and extruding fibers from said solution by means of a dry-wet spinning process or a melt-blown process. In this regard, an organic solvent is understood to be a mixture of an organic chemical and water. At present, N-methyl-morpholine-N-oxide (NMMO) is used as an organic solvent on a commercial scale.

In said process, the solution of the cellulose is usually extruded by means of a forming tool, whereby it is moulded. Via an air gap, the moulded solution gets into a precipitation bath, where the moulded body is obtained by precipitating the solution. The moulded body is washed and optionally dried after further treatment steps. A process for the production of Lyocell fibers is described, for instance, in U.S. Pat. No. 4,246,221. Lyocell fibers are distinguished by a high tensile strength, a high wet-modulus and a high loop strength.

It is well-known to modify cellulosic fibers and also Lyocell fibers via the incorporation of various additives.

In this respect, EP 1 259 564 B1 discloses Lyocell fibers which contain a material of sea plants or shells of sea animals. As sea plants, mussels are mentioned amongst others. Shells of mussles, however, contain all the contaminations that are deposited on the outer side of the shell, i.e. the side being in contact with the water.

CN 1772980 A discloses a viscose fiber containing pearl powder.

Also CN 1450212 A discloses fibers containing pearl powder. However, the fibers mentioned in CN 1450212 A are non-cellulosic synthetic fibers.

Pearl powder (i.e. ground pearls) is well-known since long time from Chinese medicine as health- and beauty-promoting and, therefore, is used in cosmetic products. This material mainly consists of $CaCO_3$ and of proteins.

The manufacturing processes for making viscose fibers and, especially, making non-cellulosic synthetic fibers differ significantly from the manufacturing process for making Lyocell fibers. Especially, in the viscose process various substances that are detrimental to the environment must be used for the production of the spinning solution. Furthermore, the manufacturing processes of these fiber types are carried out at conditions that are detrimental to the components of the pearl powder and, therefore, reduce the yield and worsen the properties of the product, respectively. Incorporating pearl powder into non-cellulosic synthetic fibers results in a low bioavailability of the powder, because the powder is encased within the fibers and, due to the hydrophobicity of such fibers, only a limited exchange with the environment is possible. In the viscose process, on the other hand, the precipitation of the fibers in an acid precipitation bath containing $H_2SO_4$ damages the $CaCO_3$ contained in the pearl powder. In any event, the $CaCO_3$ is partly dissolved, and also one must expect partial precipitation in the form of $CaSO_4$.

Furthermore, the properties of the various fiber types differ significantly from each other.

It is an object of the present invention to provide a fiber in which pure pearl material is present with a high bioavailability and wherein said fiber can be produced with a process that preserves the pearl material as much as possible.

SUMMARY OF THE INVENTION

This object is solved by a Lyocell fiber which contains a material selected from the group consisting of pearl powder, ground nacre and mixtures thereof.

The fiber according to the present invention, thus, contains a high-purity material of pearls or nacre, respectively. Nacre and pearls, respectively, are exclusively made of the innermost layer facing the mollusc, called the hypostracum. The hypostracum, in an amount of 95%, consists of pseudo-hexagonal plates of calcium carbonate having a thickness of 500 nm and exhibiting the crystalline form of aragonite. The plates are embedded in an organic matrix of proteins and chitin. Pearls essentially consist of nacre with an amount of 80-95% $CaCO_3$ which is present in the crystalline form of aragonite, eventually with a small amount of calcite (http://de.wikipedia.org/wiki/Perle; http://de.wikipedia.org/wiki/perlmutt). Having been formed concluded in the interior of the mussel (shell), the pearl—in contrast to mussle shells as a whole—develops protected from detrimental influences of the environment and therefore does not contain contaminations.

The material of pearls or nacre, respectively, may preferably be present in an amount of from about 0.07 wt. % to about 5 wt. %, based on fiber.

It is especially preferred that the material is an ultra-fine powder having an average particle size of from about 0.04 to about 1.5 µm, preferably 0.4 to 1.0 µm. Such powders are commercially available under the name "Nano-Pearl-Powder" or can be manufactured by adequate grinding of pearls and/or nacre, respectively.

As is well known, the process for manufacturing Lyocell fibers, in contrast to the process for manufacturing viscose fiber, is not based on a prior derivatization and can be carried out in an environmentally sound manner.

The process for the manufacture of the Lyocell fiber according to the present invention, therefore, comprises the known steps of manufacturing a spinning solution of cellulose in an aqueous tertiary amine oxide, preferably N-methylmorpholine-N-oxide (NMMO) and spinning the spinning solution to fibers, and is characterized in that a material selected from the group consisting of pearl powder, ground nacre and mixtures thereof is admixed to the spinning solution and/or to a precursor thereof.

As a "precursor" of the spinning solution, starting and intermediate materials for the manufacture of the spinning solution are to be understood, especially the starting cellulose material employed, e.g. pulp the solvent employed (aqueous tertiary amine oxide, in the following the term "NMMO" is used as an abbreviation for all suitable amine oxides)

a mixture of the starting cellulose material with the solvent NMMO, especially a suspension of the cellulose in an aqueous NMMO, starting from which the solution can be made.

DETAILED DESCRIPTION OF THE INVENTION

The material of pearls and/or nacre may preferably be admixed in an amount of from about 0.1 wt. % to about 5 wt.

%, based on cellulose. Typical losses of yield can be observed in an amount of from about 5 to about 30%, especially only about 10%.

The material preferably is employed in the form of a powder. Preferably the average particle size of the powder ranges from about 0.04 to about 1.5 µm, especially preferred 0.4 to 1.0 µm.

Prior to being admixed to the suspension or the precursor thereof, respectively, the powder may preferably be converted into the form of an aqueous suspension. This suspension is then admixed.

The present invention, furthermore, relates to the use of the Lyocell fiber according to the invention as a product with cosmetic effect in a textile article and/or in a non-woven cosmetic product.

Pearl powder has been referred to as being effective for softening the skin, regenerating skin cells, inhibiting melanin synthesis and, therefore, inhibiting the forming of age spots, and also sometimes as having antioxidative effect. The spectrum of effects can be ascribed to the topical application of bioavailable essential amino acids and trace elements.

With regard to the use as a cosmetic it has been shown that particle sizes in the nano-region (40-80 nm) increase the absorption speed of Ca and amino acids through the skin, as compared with particles in the micrometer size (http://www.karipearl.com/medicine.html).

The purity and the special composition of essential amino acids, mineral compounds, trace elements and the high amount of calcium render the pearl and the nacre, respectively, especially valuable for the skin.

The material of pearls and/or nacre which is incorporated into the Lyocell fiber is able, via a slow-release effect, to release steadily, and in small doses, mineral compounds, essential amino acids and calcium to the skin. Thus, the skin is continuously supplied with these micronutrients.

EXAMPLES

General Method:

The fiber according to the invention can be produced by admixing 0.5 to 5% of a powder of ground pearls (in the following referred to as "Nano Pearl Powder") into the Lyocell spinning dope and spinning the dope by employing common spinning parameters. It was found that the admixing has no significant effect on the stability of the spinning dope.

Example 1

Spinning in a Davenport Apparatus

Production of the Spinning Dope:

3 wt. % (based on the weight of cellulose) Nano Pearl Powder were admixed into a spinning dope as follows: 0.78 g Nano Pearl Powder (manufacturer: Messrs. Fenix, particle size according to the product information: 40 nm to 80 nm) were slurried in 5 ml de-ionized water in an ultrasonic bath.

For making the solution, first about 50% aqueous NMMO were mixed in a manner known per se with a stabilizer (0.1%). Afterwards the slurry of Nano Pearl Powder was admixed and finally the pulp was added. The mixture was mixed for 1 h at room temperature and 250 mbar and then heated to 70° C. Afterwards the solution was produced in a manner known per se by evaporating water. The solution was heated for some more time. The resulting solution is optically clear and free from particles >3 µm.

The solution contained 77% NMMO, 13% cellulose, 10% water, 0.1% stabilizer (all based on weight of the solution) and 3 wt. % Nano-Pearl-Powder (based on weight of cellulose).

The solution was spun by means of a Davenport spinning apparatus in a manner known per se through a spinneret at 115° C. and via an air gap. The spinneret employed had a hole diameter of 100 µm.

The fibers produced were washed in a manner known per se and cut.

The resulting fiber hat a fineness of 1.35 dtex and exhibited satisfactory tenacity properties.

Analysis of the raw material (Nano Pearl Powder) and the fiber produced therefrom gave the following results:

| Sample | Al [mg/kg] | Ca [mg/kg] | Fe [mg/kg] | Mg [mg/kg] | Mn [mg/kg] | Na [mg/kg] | Ni [mg/kg] | P [mg/kg] | S [mg/kg] | Si [mg/kg] | Zn [mg/kg] |
|---|---|---|---|---|---|---|---|---|---|---|---|
| Nano-Powder | 290 | 400000 | 450 | 43 | 740 | 3100 | 48 | 140 | 240 | 4000 | 3.9 |
| Fibre | 4.4 | 7100 | 17 | 9.2 | 12 | 47 | 1.3 | 3.4 | 44 | 82 | 4.4 |

Example 2

Spinning in a Small Pilot Plant

A spinning solution was produced, having the following composition:

13% pulp
10.5% H$_2$O
76.5% NMMO
3% Nano Pearl Powder (based on weight of cellulose)

The spinning solution, furthermore, contained a stabilizer as known per se.

The Nano Pearl Powder was first dispersed in 78% NMMO by means of an Ultra Turrax T 50 mixer. Then the pulp was added, a suspension was prepared, and a solution was produced from the suspension in a manner known per se.

The ready solution was spun at a spinning temperature of 120° C. The resulting fiber had a fineness of 1.35 dtex and exhibited satisfactory tenacity properties.

Balance of Calcium Yield

The Nano Pearl Powder employed contains 40% calcium. A loss of calcium in the washing baths in an amount of 12.7% was determined.

What is claimed is:

1. A Lyocell fiber, comprising a material selected from the group consisting of pearl powder, ground nacre and mixtures thereof, wherein the material is present in an amount of from about 0.07 wt. % to about 5 wt. %, based on fiber, and wherein loss of yield of the material during production of the fiber is from about 5% to about 30%.

2. The Lyocell fiber according to claim 1, wherein the material has an average particle size of from 0.04 to 1.5 µm.

3. A process for the manufacture of a Lyocell fiber, comprising the steps of manufacturing a spinning solution of cellulose in an aqueous tertiary amine oxide, preferably N-methylmorpholine-N-oxide (NMMO); and spinning the spinning solution to fibers, wherein a material selected from the group consisting of pearl powder, ground nacre and mixtures thereof is admixed to the spinning solution and/or to a precursor thereof, wherein the material is present in the fiber in an amount of from about 0.07 wt. % to about 5 wt. %, based on fiber, and wherein loss of yield of the material during production of the fiber is from about 5% to about 30%.

4. The process according to claim 3, wherein the material is admixed in an amount of from about 0.1 wt. % to about 5 wt. %, based on cellulose.

5. The process according to claim 3 or 4, characterized in that the material is employed in the form of a powder with an average particle size of from about 0.04 to about 1.5 µm.

6. The process according to claim 5, wherein the powder is converted into the form of an aqueous suspension prior to being admixed to the spinning solution or the precursor thereof, respectively.

7. A product comprising the Lyocell fiber according to claim 1, wherein the Lyocell fiber provides cosmetic effect in an article selected from the group consisting of a textile article and a non-woven cosmetic product.

8. A product comprising the Lyocell fiber according to claim 2, wherein the Lyocell fiber provides cosmetic effect in an article selected from the group consisting of a textile article and a non-woven cosmetic product.

9. The Lyocell fiber according to claim 2, wherein the material has an average particle size of from 0.4 to 1.0 µm.

10. The Lyocell fiber according to claim 1, wherein the loss of yield of the material during production of the fiber is about 10%.

11. The process according to claim 5, characterized in that the material is employed in the form of a powder with an average particle size of from 0.4 to 1.0 µm.

* * * * *